United States Patent
Champie

(10) Patent No.: US 12,274,713 B2
(45) Date of Patent: Apr. 15, 2025

(54) NUTRACEUTICAL COMPOSITION COMPRISING A WATER-SOLUBLE FULLERENE AND A KETONE

(71) Applicant: Max C. Champie, Buena Vista, CO (US)

(72) Inventor: Max C. Champie, Buena Vista, CO (US)

(73) Assignee: Max C. Champie, Buena Vista, CO (US)

( * ) Notice: Subject to any disclaimer, the term of this patent is extended or adjusted under 35 U.S.C. 154(b) by 0 days.

(21) Appl. No.: 17/738,801

(22) Filed: May 6, 2022

(65) Prior Publication Data
US 2022/0354886 A1    Nov. 10, 2022

Related U.S. Application Data

(60) Provisional application No. 63/273,009, filed on Oct. 28, 2021, provisional application No. 63/185,540, filed on May 7, 2021.

(51) Int. Cl.
| | | |
|---|---|---|
| *A61K 33/44* | (2006.01) | |
| *A61K 47/54* | (2017.01) | |
| *A61K 47/69* | (2017.01) | |
| *A61P 25/28* | (2006.01) | |

(52) U.S. Cl.
CPC ............ *A61K 33/44* (2013.01); *A61K 47/542* (2017.08); *A61K 47/6923* (2017.08); *A61P 25/28* (2018.01)

(58) Field of Classification Search
CPC .. A61K 33/44; A61K 47/6923; A61K 47/542; A61P 25/28
See application file for complete search history.

(56) References Cited

U.S. PATENT DOCUMENTS

| | | |
|---|---|---|
| 6,777,445 B2 | 8/2004 | Lei |
| 7,163,956 B2 | 1/2007 | Wilson |
| 10,239,839 B2 | 3/2019 | Kronholm |
| 2003/0162837 A1 | 8/2003 | Dugan |
| 2014/0140985 A1 | 5/2014 | Moussa |

FOREIGN PATENT DOCUMENTS

| | | | |
|---|---|---|---|
| WO | WO 2009114087 | * | 12/2009 |
| WO | 2013025180 | | 2/2013 |

OTHER PUBLICATIONS

Patricio et al. Frontiers in Pharmacology (2020) 1-24.*
Rasovic (Materials Science and Technology 33:7, 777-794).*
Hsieh et al. (ACS Appl. Mater. Interfaces (2017); 9;13, 11482-11492).*
Rasovic (Materials Science and Technology 33:7, 777-794); 2017.*
Chistyakov, et al. "Possible Mechanisms of Fullerene C60 Antioxidant Action," BioMed Research International vol. 2013, Article ID 821498, 4 pages.
Grebowski, et al. "Fullerenols as a New Therapeutic Approach in Nanomedicine," BioMed Research International vol. 2013, Article ID 751913, 9 pages.
Hsieh, et al. "Water-Soluble Fullerene Derivatives as Brain Medicine: Surface Chemistry Determines If They Are Neuroprotective and Antitumor," ACS Appl. Mater. Interfaces 2017, 9, 13, 11482-11492. 10 pages.
Wikipedia, "Ketone Bodies." https://en.wikipedia.org/w/index.php?title=Ketone_bodies&oldid=1018905478 7 pages.
S Nakamura and T Mashino 2009 J. Phys.: Conf. Ser. 159 012003. "Biological activities of water-soluble fullerene derivatives." 9 pages.
Prylutska, et al. "Pristine C60 Fullerenes Inhibit the Rate of Tumor Growth and Metastasis," Exp Oncol 2011 33, 3, 162-164. 3 pages.
Quick, et al. "A carboxyfullerene SOD mimetic improves cognition and extends the lifespan of mice," Neurobiology of Aging 29 (2008) 117-128. 12 pages.
Solaris Chem. www.solarischem.com. 4 pages.
Wharton, et al. "New non-ionic, highly water-soluble derivitives of C60 designed for biological compatibility," Tetrahedron Letter, vol. 42, Issue 31, Jul. 2001. 3 pages.

* cited by examiner

*Primary Examiner* — Shirley V Gembeh
(74) *Attorney, Agent, or Firm* — Fish IP Law, LLP

(57) ABSTRACT

Compositions and methods are described in which a water-soluble fullerene (preferably a water-soluble buckminsterfullerene or C60) is used in combination with an associated ketone in order to treat central nervous system disease or injury. The associated ketone can be noncovalently coupled to the outer surface of the water-soluble fullerene, covalently coupled to the outer surface of the water-soluble fullerene, and/or encapsulated or otherwise held within the interior volume of the water-soluble fullerene. Such formulations are effective in increasing neuronal activity in damaged portions of the central nervous system, reduce fatigue, and increase endurance.

7 Claims, 8 Drawing Sheets

NUTRACEUTICAL COMPOSITION COMPRISING A WATER-SOLUBLE FULLERENE AND A KETONE

This application claims the benefit U.S. Provisional Patent Application No. 63/185,540 filed on May 7, 2021, and U.S. Provisional Patent Application No. 63/273,009, filed Oct. 28, 2021. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is nutraceutical compositions, especially compositions containing fullerene.

BACKGROUND

The following description includes information that may be useful in understanding the present invention. It is not an admission that any of the information provided herein is prior art or relevant to the presently claimed invention, or that any publication specifically or implicitly referenced is prior art.

The following description includes information that may be useful in understanding the present invention. It is not an admission that any of the information provided herein is prior art or relevant to the presently claimed invention, or that any publication specifically or implicitly referenced is prior art.

The human body is under constant attack from oxidative stress caused by free radicals from e.g., reactive oxygen species (ROS). Oxidative stress causes damage to cells, especially cellular protein and DNA, and is associated with many human diseases, including cancer, atherosclerosis, Alzheimer's disease, and Parkinson's disease. Oxidative stress also contributes to aging, which can be defined as a gradual accumulation of free-radical damage.

Buckminsterfullerene is a fullerene with the formula C60. It has a cage-like fused-ring structure (truncated icosahedron) that resembles a soccer ball, made of twenty hexagons and twelve pentagons, with a carbon atom at each vertex of each polygon and a bond along each polygon edge. Due to its 30 carbon double bonds, 60-carbon fullerene is a powerful and recyclable antioxidant that neutralizes harmful free radicals. It is reported to be 172 times more potent than Vitamin C, working as an electron reservoir to defuse reactive oxygen species (ROS) in the body, without altering its own structure.

A novel mechanism of antioxidant activity of buckminsterfullerene C60, based on protons absorbing and mild uncoupling of mitochondrial respiration and phosphorylation, was confirmed by computer modeling using Density Functional Theory. According to the model, Fullerene's geroprotective activity is significantly higher than those of the most powerful reactive oxygen species scavengers. C60 has an apparent ability to acquire positive charge by absorbing several protons, and this complex can then penetrate into mitochondria. Such a process allows for mild uncoupling of respiration and phosphorylation, which in turn leads to decrease in ROS production. See "Possible Mechanisms of Fullerene C60 Antioxidant Action," Chistyakov et al., BioMed Research International, vol. 2013, Article ID 821498, 4 pages, 2013.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Presumably due to its anti-oxidant and anti-aging properties, C60 and its derivatives have been shown to prolong life in a variety of species, including mice (Quick et al., "A carboxy-fullerene SOD mimetic improves cognition and extends the lifespan of mice" Neurobiology of Aging 29 (2008) 117-128) and rats (Baati et al., "The prolongation of the lifespan of rats by repeated oral administration of [60] fullerene," Biomaterials 33 (2012) 4936-4946). C60 fullerene was also shown to inhibit tumor growth and metastasis. See Prylutska et al., Pristine C60 Fullerenes Inhibit the Rate of Tumor Growth and Metastasis. Exp Oncol 2011, 33, 3, 162-164.

Unfortunately, the biomedical uses of conventional C60 fullerenes are severely limited their very limited solubility. Fullerene derivatives have been developed that have varying degrees of solubility in water and that show promise in medicinal formulations (Grebowski et al., BioMed Research International, Vol. 2013, Article ID 751913). For example, a C60 fullerene with four pendant 2-amino-1,3 propanediol groups have been found to be water soluble and biologically active (Wharton et al., Tetrahedron Letters, 42:5159-5162 (2001). Similarly, Hsieh et al. (ACS Appl. Mater. Interfaces, 9: 11482-11492 (2017)) have identified C60 fullerenes derivatized using specific covalent linkages that are both water soluble and show a degree of selectivity.

Beta-hydroxybutyrate (BHB), also known as 3-hydroxybutyric acid or 3-hydroxybutanoic acid (3HB), is the most abundant ketone body compounds (i.e., a compound produced by the body when it is metabolizing fat), accounting for 78% of total ketones in the blood. Other ketone body compounds include acetoacetate (AcAc), which makes up approximately 20% of ketones in the blood, and acetone. Although both BHB and acetone are derived from acetoacetate (AcAc), BHB is the primary ketone used for energy because it's extremely stable and abundant. There are two isomers of BHB that made by the body: D-BHB and L-BHB. D-BHB is used for efficient energy production and is produced in high amounts; it is responsible for the anti-aging effects of total BHB. L-BHB is produced in small quantities and can't be used for energy as efficiently as D-BHB; it is utilized in the synthesis of fatty acids.

Previous work has used C60 or its derivatives for health benefits. For example, U.S. Patent Application Publication No.: US 2014/0140985, and PCT Publication No. WO 2013/025180, both by Moussa et al., teach using fullerene partially dissolved in a lipid carrier to prolong the life span in rats. U.S. Patent Application Publication No.: US 2003/0162837, by Dugan et al., teaches increasing a metazoan's lifespan by administering a carboxylated derivative of a C60 fullerene. U.S. Pat. No. 6,777,445 to Lei et al. teaches using fullerene to treat certain bacterial and viral infections. U.S. Pat. No. 7,163,956 to Wilson et al. and U.S. Pat. No. 10,239,839 to Kronholm et al. teach using substituted fullerene composition as antioxidants and for radical scavenging.

However, none of these references teach using a water-soluble buckminsterfullerene (C60) in combination with ketones (e.g., ketones body compounds) to treat central nervous system conditions.

Thus, there is a need for improved fullerene molecule compositions that are effective to treat central nervous system conditions.

SUMMARY OF THE INVENTION

The inventive subject matter provides compositions that include a water-soluble fullerene (such as buckminsterfullerene or C60) and a ketone, as well as their use in treating neurological diseases, injuries, and/or conditions.

Embodiments of the inventive concept include composition that are useful in treatment of a central nervous system condition. Such compositions include a water-soluble fullerene and a ketone. The water-soluble fullerene and the ketone are provided in a ratio that is effective to treat the central nervous system condition. Suitable ketones include ketone body compounds, such as acetoacetate, beta hydroxybutyric acid, beta ketopentanoate, and beta hydroxypentanoate. In some embodiments such a ketone can include an ester. The ketone can be reversibly coupled to the water-soluble fullerene, covalently coupled to the water-soluble fullerene, and/or encapsulated within the water-soluble fullerene. In some embodiments such a composition provides a synergistic effect in treating the central nervous system condition that exceeds additive effects of the water-soluble fullerene and the ketone when applied individually.

Other embodiments of the inventive concept include methods of treating a central nervous system condition (such as a central nervous system cancer, a neurodegenerative disease, a stroke, a bacterial infection, a viral infection, a fungal infection, intoxication, a condition resulting from oxidative stress, decreased cognitive function, fatigue, impaired memory, and/or reduced alertness) by applying a composition as described above to an individual in need of treatment for the central nervous system condition, in an amount and on a schedule that is effective in treating the central nervous system condition. Treatment can include oral administration, subcutaneous injection, intramuscular injection, intravascular injection, infusion, topical application, and/or inhalation of a compound or formulation as described above.

Other methods of the inventive concept include methods for increasing activity in damaged or quiescent central nervous system neurons (for example, neurons impacted by a stroke, a cerebrovascular accident, and/or traumatic brain injury) by administering, to an individual in need of treatment, a composition that includes a water-soluble fullerene and a ketone, where the water-soluble fullerene and the ketone are provided in a ratio that is effective to increase activity in a quiescent neuron of the individual's central nervous system. Such a ketone can be a ketone body compound, and/or include an ester. Such a ketone can be reversibly coupled to the water-soluble fullerene, covalently coupled to the water-soluble fullerene, and/or encapsulated by the water-soluble fullerene.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 shows the structure of an exemplary water-soluble fullerene.

FIG. 2 shows the structures of exemplary water-soluble fullerenes.

FIG. 3 shows an exemplary ketone structure.

FIG. 4 shows an exemplary ketone structure that includes an ester bond.

FIG. 5 shows a topographic heatmap of maximum P300 evoked reaction potential of an individual who has suffered a stroke, both before (session 1) and 30 minutes after (session 2) treatment with a formulation of the inventive concept.

FIG. 6 shows data from individual contacts utilized in the study of FIG. 5, where blue lines represent pre-treatment data and red lines represent post-treatment data.

FIGS. 7A and 7B show Z scores for theta, alpha, and beta wave activity at each contact in the study of FIG. 5, as well as coherence between different regions. FIG. 7A depicts pre-treatment results. FIG. 7B depicts results from 30 minutes post-treatment with a formulation of the inventive concept.

FIGS. 8A and 8B show results of brain activity scans of an individual with autism. FIG. 8A depicts pre-treatment results. FIG. 8B depicts results from 30 minutes post-treatment with a formulation of the inventive concept.

DETAILED DESCRIPTION

Figure 1:
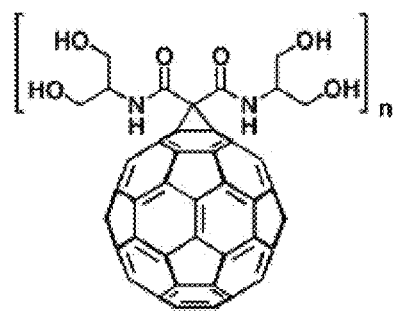
FIG. 1.

The inventive subject matter provides apparatus, systems and methods in which a water-soluble fullerene (preferably a water-soluble buckminsterfullerene or C60) is used in combination with an associated ketone (preferably a ketone body molecule such as beta hydroxybutyrate) to the use of such a compound to treat central nervous system disease and/or condition. The associated ketone can be noncovalently coupled to the outer surface of the water-soluble fullerene, covalently coupled to the outer surface of the water-soluble fullerene, and/or encapsulated or otherwise held within the interior volume of the water-soluble fullerene. Oils and similar solubility enhancers are not needed in such formulations.

Free radicals are highly reactive compounds with one or more unpaired valence electrons. Conventional antioxidants donate an electron to complete the pair and render such a compound relatively nonreactive. Antireductants, on the other hand, can accept an electron to eliminate free radicals and make the molecule less reactive. Free-radical containing compounds are critical for number of metabolic reactions, however they can be enormously destructive when they occur outside of such metabolic reactions.

The electrons responsible for forming unwanted free radicals can be a result of the normal process of respiration via the mitochondrial electron transport chain. D-beta-hydroxybutyrate, the primary ketone produced by the liver, is unique in that it can both accept an electron from a free radical and return it to the electron transport chain in order for it to be used by the body as energy. Fullerenes, such as C60, can act as a 'sponge' or repository for electrons derived from free radicals. Without wishing to be bound by theory, the inventor believes that ketones (such as hydroxybutyrate) and fullerenes can be used in concert to capture electrons from unwanted free radicals and shunt them to the mitochondrial electron transport chain, where they can be utilized to generate energy for the cell. Unfortunately, the utility of conventional fullerenes for such a purpose is limited by their lack of solubility. While oils or similar solvent systems can improve conventional fullerene solubility, it is not clear that fullerenes so solubilized, which are likely in micellar suspension rather than true solution, can be provided in adequate quantities or can penetrate cell membranes, intracellular membranes (such as those encompassing mitochondria) and/or tissue barriers (such as the blood brain barrier).

The inventor has surprisingly found that both ketones and water-soluble fullerenes (such as polyhydroxylated C60) can pass through cell membranes, mitochondrial membranes, and the blood brain barrier. The inventor believes that this advantageously provides access to both regions of the body that are generally considered difficult to access safely for treatment (e.g., the central nervous system) and the mitochondria where free radicals are created. While the cell's cytosol normally contains antioxidants and antireductants, by the time free radicals reach this part of the cell they can already have damaged the mitochondria-resulting in decreased energy production (e.g., ATP production) within the cell. The inventor believes that such damaged mitochondria can continue to produce damaging free radicals, setting in to place a cycle of increasing damage and reduced ATP production within the cell.

Without wishing to be bound by theory, the inventor believes that this destructive cycle can be reduced or eliminated through the use of a combination of a water soluble fullerene (which provides a repository for electrons obtained from free radicals) and a suitable ketone (which can effectively return such electrons to the respiratory chain)—with the use of water soluble fullerenes providing access to both appropriate cellular compartments and to tissues that are generally considered difficult to treat due to the presence of tissue barriers (e.g., the blood brain barrier). The inventor believes that cells of the central nervous system are particularly suited for utilizing ketones in this fashion.

The Inventor has found that conventional, water-insoluble fullerene in combination with a ketone compound can be used to treat central nervous system disorders and/or diseases, for example providing improved memory, alertness, and/or cognitive skills in persons with Alzheimer's disease and other neurodegenerative conditions. Surprisingly, the Inventor has found that the use of a water-soluble fullerene in combination with the ketone compound provides a similar beneficial effect that is a duration that is increased by a factor of 2-fold, 3-fold, 4-fold, 5-fold or more relative to corresponding treatment using the water-insoluble fullerene/ketone mixture. The Inventor believes that similar benefits are realized in treatment of transient central nervous system impairments, such as those due to fatigue, stress, infectious disease, and/or intoxication.

Without wishing to be bound by theory, the Inventor believes that ketones (such as a ketone body compound) have a beneficial effect on activity of neurons that are damaged or otherwise rendered quiescent by injury, disease, and/or external factors (such as intoxication, fatigue, etc.), however these benefits are not realized by administration of ketones alone as they fail to cross the blood brain barrier. Inventor has found that water-soluble fullerenes (such as a water soluble buckminsterfullerene or C60) can facilitate transport of ketone compounds across the blood brain barrier. Inventor has also found that water-soluble fullerenes are readily excreted through the kidneys, rendering them non-toxic and safe for use.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

One embodiment of the inventive concept is a composition that is useful for the treatment of a central nervous system disease and/or condition. Such a composition can include a water-soluble fullerene and a ketone. In such a composition the water-soluble fullerene, the ketone, and/or the ratio between them are selected and provided to be effective to treat the central nervous system condition.

Figure 2:
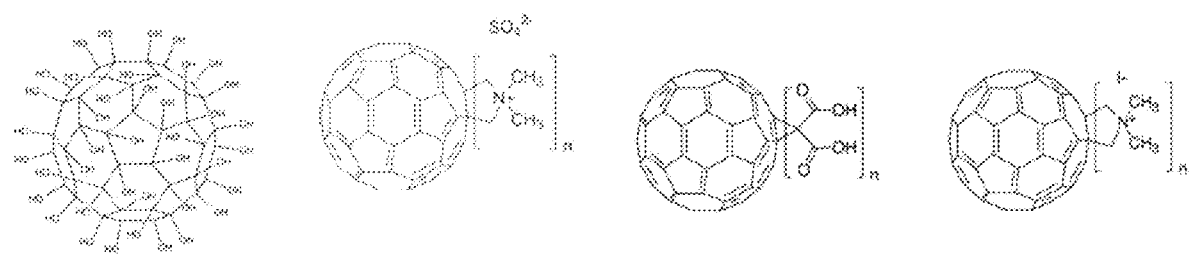
FIG. 2.

The water-soluble fullerene can include one or more pendant hydrophilic moiety(ies) that provide solubility in aqueous solutions. For example, such a pendant hydrophilic moiety can be a cationic group, an anionic group, a hydroxy or polyhydroxy group, and/or an amino acid side-chain group. Examples of water-soluble fullerenes are provided in FIGS. 1 and 2.

Figure 3:
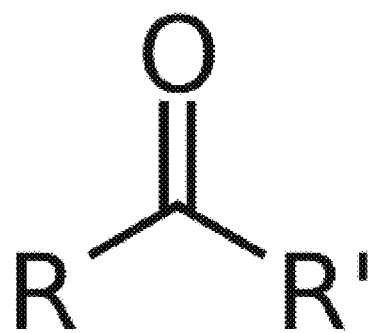
FIG. 3.
Figure 4:
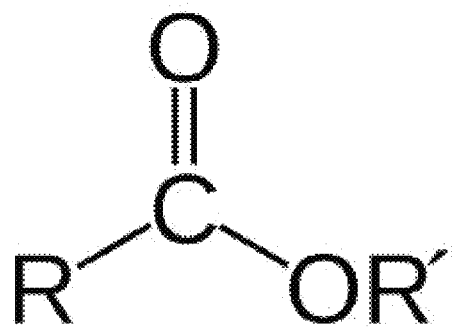
FIG. 4.

Ketone compounds of the inventive concept include compounds characterized by the presence of the chemical structure shown in FIG. 3. Ketones of the inventive concept also include compounds associated with ketone bodies (ketone body compounds), which are typically produced during metabolism of fats. Suitable ketone body compounds include acetoacetate, beta hydroxybutyric acid, beta ketopentanoate, beta hydroxypentanoate, and mixtures thereof. In some embodiments the ketone compound can include an ester group, as shown in FIG. 4.

In preferred embodiments, the ketone or ketone body compound is provided as a ketone ester. In such embodiments the ketone or ketone body compound (e.g., beta hydroxybutyrate) can be esterified to a ketone precursor compound (e.g., butanediol, glycerol, etc.). Following administration of the formulation such an ester bond will typically hydrolyze over time, which the Inventor believes provides a prolonged or enhanced effect. In some embodiments the ketone or ketone body compound is beta hydroxybutyrate.

In some embodiments an ester group or similarly scissile group can provide a linkage group that intervenes between the C60 fullerene structure and the pendant hydrophilic group. In other embodiments the ester group can be positioned within the pendant hydrophilic group that confers solubility in aqueous solutions.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In compositions of the inventive concept the ketone can be reversibly coupled to the water-soluble fullerene. Such a reversible linkage can be covalent (e.g., a scissile covalent bond between the ketone and the water-soluble fullerene) or noncovalent (e.g., a hydrogen bond, Van der Waals, and/or hydrophobic interaction between the ketone and the water-soluble fullerene). In some embodiments the ketone is coupled to the water-soluble fullerene via an ester bond, which can be selected to be reversible. In some embodiments, at least a portion of the ketone portion of the composition is encapsulated within the water-soluble fullerene (i.e., is located within the interior cavity of the C60 portion of the water-soluble fullerene).

As noted above, compositions of the inventive concept are useful in treating central nervous system conditions. In some embodiments the central nervous system condition is a result of disease. For example, compositions of the inventive concept can be used to treat a central nervous system cancer, such as an astrocytoma, a meningioma, an oligodendroglioma, an ependymoma, mixed glioma, a mixed glioma and neuronal tumor, and a primitive neuroectodermal tumor. In some embodiments the central nervous system condition is a neurodegenerative disease, such as Alzheimer's disease and other memory disorders, ataxia, Huntington's disease, Parkinson's disease, motor neuron disease, multiple system atrophy, and progressive supranuclear palsy. In some embodiments the central nervous system condition can be the result of a stroke and/or an injury.

In other embodiments, the central nervous system condition is a result of a transient condition. Such a transient condition can be a result of infection, such as a bacterial infection, a viral infection, a parasitic infection, and/or a fungal infection. In such embodiments application of a composition of the inventive concept can be elimination or reduction of the time course of the infection. Alternatively, application of a composition of the inventive concept can improve central nervous system-associated symptoms of the infection, such as improving alertness, cognitive function, and/or memory. Such improvements can be characterized using conventional tests of cognitive functions and/or recall.

Other transient conditions can be a result of environmental factors, for example fatigue, anxiety, psychological stress, oxidative stress, and/or intoxication. In such embodiments application of a formulation of the inventive concept can act to reduce cognitive deficits resulting from such environmental factors, such as improving alertness, memory, and/or cognitive functions. Such improvements can be characterized using conventional tests of cognitive functions and/or recall.

As noted above, formulations of the inventive concept include both a water-soluble fullerene and a ketone (preferably a ketone body compound) in combination. Such formulation can be provided any form suitable for administration by the selected route. For example, a formulation of the inventive concept can be provided as a liquid (e.g., a solution, suspension, or micellar suspension), an aerosol, or a solid (e.g., a powder, a tablet, a pill, a capsule, an implant, or a suppository). A formulation of the inventive concept can be provided in a ready to use form or can be provided as a kit. Such a kit can provide the formulation in two or more parts that are combined prior to use (e.g., a water-soluble fullerene composition, a ketone composition, and, optionally, a diluent).

In some embodiments of the inventive concept, compositions or formulations intended for oral administration can include a flavorant (e.g., a sweetener) or masking agent (e.g., a vanilla flavor) in order to improve palatability. Sweeteners of such an embodiment can be natural or artificial, and can be caloric or non-caloric. Preferred sweeteners include stevia and xylitols.

A formulation of the inventive concept can provide the water-soluble fullerene and ketone components in any suitable molar ratio. For example, the molar ratio of water-soluble fullerene to ketone can be 1:1, 1:3, 1:6: 1:10, 1:30, 1:60, 1:100, 1:300, 1:1,000, 1:3,000, 1:6,000, $1:10^4$; $1:3\times10^4$; $1:6\times10^4$, $1:10^5$, $1:3\times10^5$, $1:6\times10^5$, $1:10^6$, 1: greater than $10^6$, or any intermediate value or range. In preferred embodiments the weight ratio of water soluble fullerene to D-butylhydroxybutyrate ketone can range from 1:1 to 1:50,000.

Another embodiment of the inventive concept is a method of treating a central nervous system disorder using a composition or formulation as described above. In some embodiments the composition or formulation provides a synergistic effect in treating the central nervous system condition that exceeds additive effects of the water-soluble fullerene and the ketone when applied individually. In such methods a composition as described above can be administered to an individual in need of treatment for the central nervous system condition in an amount and on a schedule effective to treat the central nervous system condition. Such an amount or schedule can be derived from historical data (e.g., clinical studies) or can be determined on individual basis (e.g., by applying a baseline dosage and schedule, evaluating the effect on the individual's central nervous system condition, and adjusting the dosage and/or schedule accordingly).

Methods of the inventive concept can be utilized in the treatment of one or more central nervous system conditions. In some embodiments the central nervous system condition is a result of disease. For example, compositions of the inventive concept can be used to treat a central nervous system cancer, such as an astrocytoma, a meningioma, an oligodendroglioma, an ependymoma, mixed glioma, a mixed glioma and neuronal tumor, and a primitive neuroectodermal tumor. In such embodiments a method of the inventive concept can include cotherapy with a conventional anti-cancer therapy, such as chemotherapy, radiation therapy, hyperthermia therapy, and/or immunotherapy. In some embodiments the central nervous system condition is a neurodegenerative disease, such as Alzheimer's disease and other memory disorders, ataxia, Huntington's disease, Parkinson's disease, motor neuron disease, multiple system atrophy, and progressive supranuclear palsy. In such embodiments a method of the inventive concept can include cotherapy with conventional treatments for such conditions. Such cotherapies can provide synergistic effects that exceed the additive effects of therapy with the water-soluble fullerene/ketone formulation and the conventional therapy when applied individually. In some embodiments the central nervous system condition can be the result of a stroke and/or an injury.

In other embodiments, the central nervous system condition is a result of a transient condition. Such a transient condition can be a result of infection, such as a bacterial infection, a viral infection, a parasitic infection, and/or a fungal infection. In such embodiments application of a composition of the inventive concept can be elimination or reduction of the time course of the infection. In some embodiments the method includes cotherapy with a conventional antibacterial, antiviral, antiparasitic, and/or antifungal agent. Alternatively, application of a composition of the inventive concept can improve central nervous system-associated symptoms of the infection, such as improving alertness, cognitive function, and/or memory. In some embodiments the method includes cotherapy with a conventional pharmaceutical agent used to treat such issues, such as a stimulant or an acetylcholinesterase inhibitor. Such improvements can be characterized using conventional tests of cognitive functions and/or recall. In such embodiments the method can provide synergistic effects that exceed the additive effects of treatment with the water-soluble fullerene/ketone formulation and the conventional therapy when applied individually.

Other transient conditions can be a result of environmental factors, for example fatigue, anxiety, psychological stress, oxidative stress, and/or intoxication. In such embodiments application of a formulation of the inventive concept can act to reduce cognitive deficits resulting from such environmental factors, such as improving alertness, memory, and/or cognitive functions. Such improvements can be characterized using conventional tests of cognitive functions and/or recall.

In methods of the inventive concept, a formulation as described above can be administered to an individual in need of treatment in any suitable fashion. For example, a formulation that includes a water-soluble fullerene and a ketone can be administered orally (e.g., by ingestion), by injection (e.g., subcutaneous injection, intramuscular injection, intravascular injection, intraperitoneal injection), infusion, topical application (e.g., to skin, mucus membrane, eye surface, etc.), and/or inhalation (e.g., of a vapor, mist, or powder). It should be appreciated that appropriate buffers, excipients, matrices, and/or stabilizers can be included based on the route of administration.

In methods of the inventive concept a composition as described above can be administered on any suitable schedule or at any suitable interval. For example, a formulation of the inventive concept can be administered to an individual in need of treatment for a central nervous system disorder at an interval of 1 hour, 2 hours, 3 hours, 4 hours, 6 hours, 8 hours, 12 hours, 24 hours, 36 hours, 48 hours, 72 hours, 7 days, 14 days, 28 days, 2 months, 3 months, 4 months, 6 months, 9 months, or annually. In some embodiments the intervals between administration can be adjusted during the course of treatment in order to accommodate improvement in or deterioration of the individual's condition or symptoms. In preferred embodiments a treatment schedule can include oral administration of about 28 grams to 850 grams, once or twice a day.

In methods of the inventive concept a compound or formulation as described above can be administered to an individual in need of treatment for a central nervous system disorder in any suitable amount. Suitable amounts, expressed in amount of formulation or composition per kg of body weight, include 0.01 mg/kg, 0.03 mg/kg, 0.1 mg/kg, 0.3 mg/kg, 1 mg/kg, 3 mg/kg, 10 mg/kg, 30 mg/kg, 100 mg/kg, 300 mg/kg, 1 g/kg, 3 g/kg, 10 g/kg, 30 g/kg, 100 g/kg, or more (inclusive of intermediate values).

Samples obtained from volunteers indicate that water-soluble fullerenes are excreted in the urine following administration of compositions of the inventive concept. There are no indications of toxicity.

EXAMPLES

Example 1

EEG data was gathered (using a WaVi device) from a 72-year-old male individual that had suffered a left side stroke three years prior. The WaVi device provides a roughly hexagonal array of contact electrodes distributed over the individual's skull and is considered suitable for monitoring electrical activity within the underlying regions of the brain. EEG activity was recorded prior to (session 1) and approximately 20 minutes following treatment with a composition of the inventive concept that included a water-soluble C60 fullerene and a ketone (session 2).

P300 voltages and P300 speeds are considered to be indicative or brain activity. In the pre-treatment scan it was apparent that most of the left side of the individual's brain showed reduced activity indicative of poor or inefficient processing. Relatively low P300 voltages were observed across the left side and rear portions of the brain. Following a single dose of a formulation of the inventive concept, the shows an increase in P300 voltage across the previously quiescent left side of the brain. Without wishing to be bound by theory, the inventor believes that this unexpected and unprecedented change is a result of delivery of the water soluble ketones and water-soluble fullerene across the blood brain barrier., we see an increase in processing voltage across all of John's left side of his brain (THIS IS NEVER SEEN). We go from not conducting signals to actually conducting voltage at some sites which is VERY interesting. We also can see that his brain became more symmetrical, as well as some of his randomized eye movement decreased which is what allowed us to pick up better data in his scan.

Figure 5:
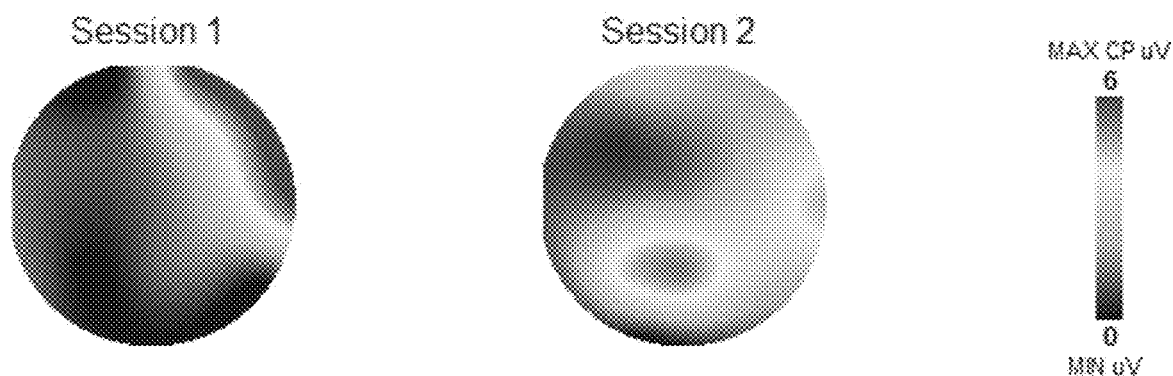
FIG. 5.

FIG. 5 shows a topographic heatmap of maximum P300 evoked reaction potential. Session 1, representing data obtained prior to treatment, shows a marked concentration of activity in areas on the right side of the brain. This is consistent with left side stroke and subsequent neuroplasticity during recovery. Surprisingly, activity is much more equally distributed between affected and unaffected areas of the brain following administration of a composition of the inventive concept.

Figure 6:
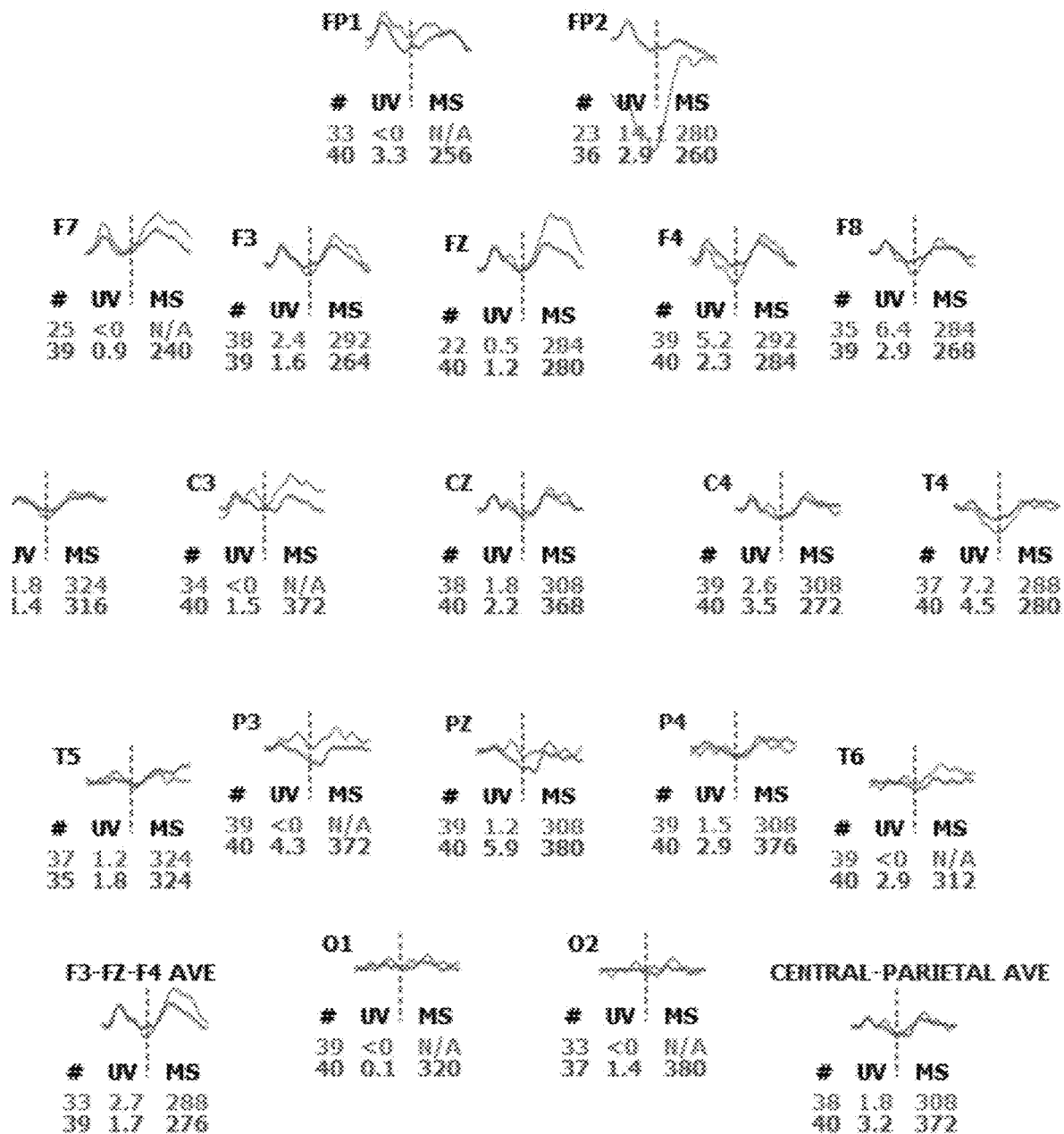
FIG. 6.
Figure 7A:
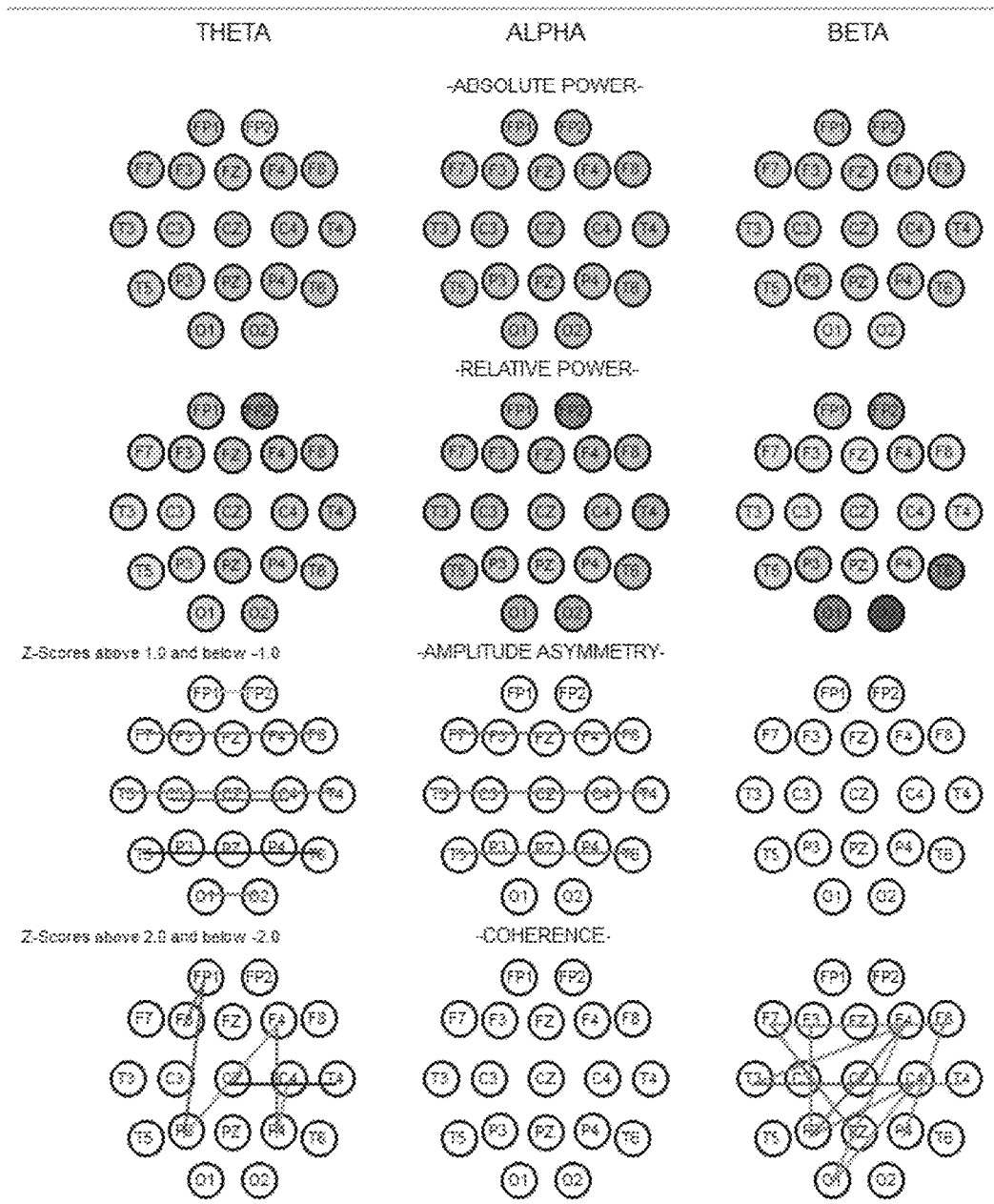
FIGS. 7A and 7B.
Figure 7B:
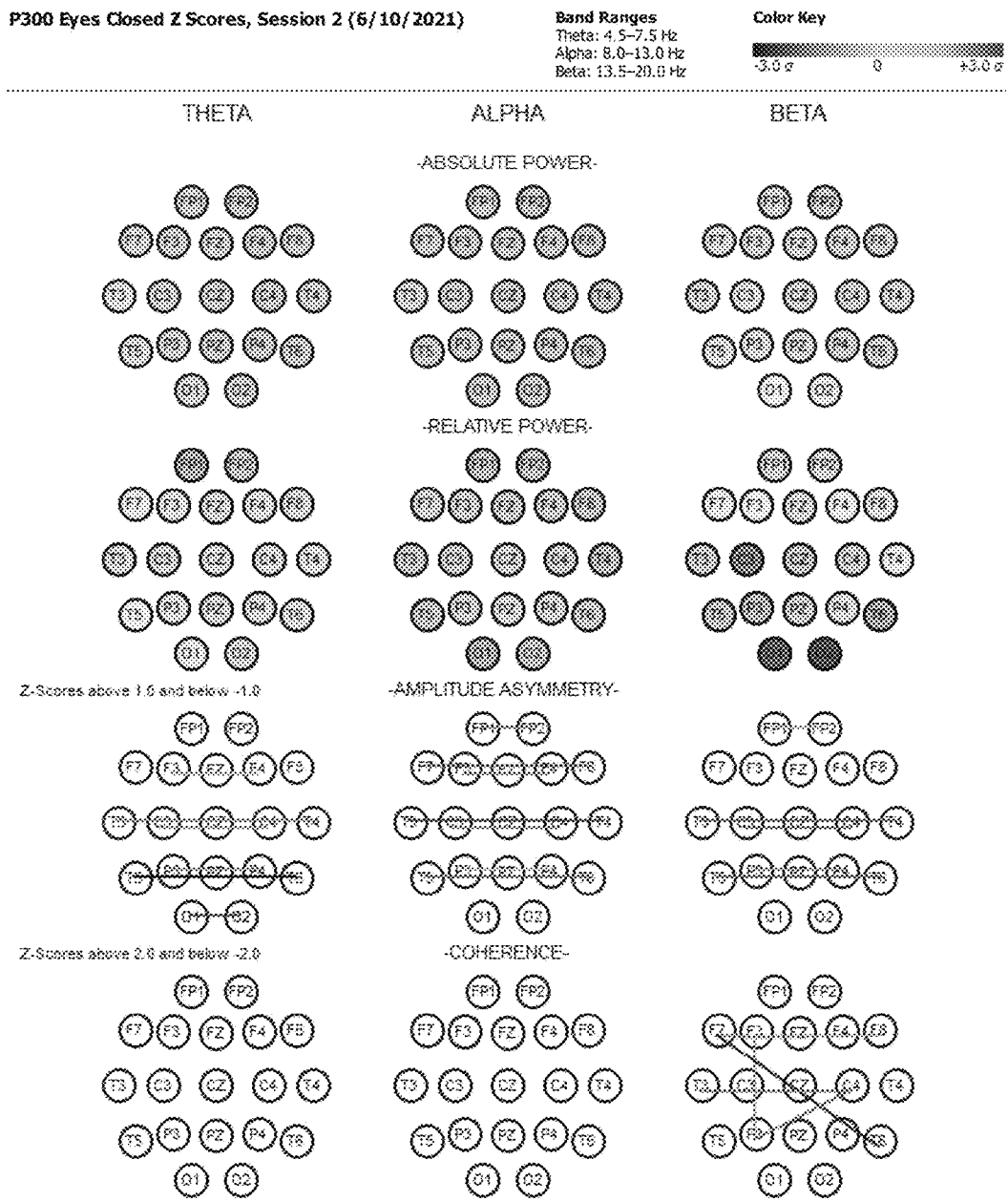

Data for individual contacts is shown in FIG. 6, where blue lines represent pre-treatment data and red lines represent post-treatment data. Z scores for theta, alpha, and beta wave activity at each contact, as well as coherence between different regions, are shown in FIG. 7A (pre-treatment) and FIG. 7B (post-treatment).

The magnitude of pre-treatment and post-treatment P300 responses in theta, alpha, and beta bands is shown in Table 1. Differences between pre-treatment and post-treatment values are evident, particularly for Beta waves at the T3 contact.

TABLE 1

| | Session 1 (pre-treatment) | | | | Session 2 (post-treatment) | | |
|---|---|---|---|---|---|---|---|
| Location | Theta | Alpha | Beta | Location | Theta | Alpha | Beta |
| FP1 | 9 | 9 | 11 | FP1 | 7 | 9 | 10 |
| FP2 | n/a | 8 | 10 | FP2 | 6 | 8 | 8 |
| F3 | 7 | 10 | 10 | F3 | 7 | 10 | 9 |
| F4 | 7 | 9 | 11 | F4 | 6 | 9 | 9 |
| F7 | 7 | 9 | 10 | F7 | 7 | 10 | 10 |
| F8 | 5 | 7 | 11 | F8 | 6 | 8 | 9 |
| C3 | 8 | 12 | 11 | C3 | 7 | 12 | 13 |
| C4 | 6 | 10 | 12 | C4 | 6 | 10 | 10 |
| P3 | 7 | 14 | 11 | P3 | 7 | 14 | 11 |
| P4 | 6 | 13 | 13 | P4 | 6 | 13 | 10 |
| O1 | 7 | 13 | 21 | O1 | 8 | 14 | 24 |

TABLE 1-continued

| | Session 1 (pre-treatment) | | | | Session 2 (post-treatment) | | |
|---|---|---|---|---|---|---|---|
| Location | Theta | Alpha | Beta | Location | Theta | Alpha | Beta |
| O2 | 6 | 15 | 31 | O2 | 6 | 13 | 26 |
| T3 | 7 | 10 | 10 | T3 | 8 | 12 | 17 |
| T4 | 5 | 7 | 12 | T4 | 5 | 7 | 11 |
| T5 | 8 | 12 | 11 | T5 | 8 | 13 | 11 |
| T6 | 4 | 9 | 14 | T6 | 4 | 9 | 10 |
| FZ | 6 | 9 | 10 | FZ | 7 | 10 | 8 |
| CZ | 7 | 12 | 10 | CZ | 7 | 13 | 8 |
| PZ | 7 | 16 | 11 | PZ | 7 | 16 | 10 |

Tables 2A and 2B show the degree of pre- and post-treatment coherence (respectively) between cited pairs of contacts. The magnitude of differences between pre-treatment data (Table 2A) and post-treatment data (Table 2B) is shown in Table 3A and Table 3B, where pre-treatment data (Table 2A) serves as the reference.

TABLE 2A

| Pair | Θ | α | β | Pair | Θ | α | β | Pair | Θ | α | β | Pair | Θ | α | β |
|---|---|---|---|---|---|---|---|---|---|---|---|---|---|---|---|
| FP1-FP2 | N/A | .72 | .66 | F3-O2 | .27 | .05 | .09 | F8-T3 | .33 | .22 | .30 | P4-T4 | .36 | .44 | .43 |
| FP1-F3 | .40 | .76 | .67 | F3-T3 | .51 | .55 | .44 | F8-T4 | .30 | .46 | .50 | P4-T5 | .48 | .30 | .36 |
| FP1-F4 | .29 | .63 | .50 | F3-T4 | .28 | .28 | .34 | F8-T5 | .19 | .07 | .30 | P4-T6 | .67 | .70 | .88 |
| FP1-F7 | .37 | .74 | .60 | F3-T5 | .35 | .24 | .47 | F8-T6 | .29 | .08 | .30 | P4-FZ | .50 | .21 | .48 |
| FP1-F8 | N/A | .56 | .41 | F3-T6 | .29 | .06 | .27 | F8-FZ | N/A | .71 | .59 | P4-CZ | .62 | .44 | .66 |
| FP1-C3 | .31 | .48 | .48 | F3-FZ | .77 | .84 | .76 | F8-CZ | .47 | .47 | .50 | P4-PZ | .78 | .79 | .86 |
| FP1-C4 | .30 | .36 | .38 | F3-CZ | .59 | .62 | .69 | F8-PZ | .33 | .16 | .41 | O1-O2 | .74 | .50 | .23 |
| FP1-P3 | .29 | .16 | .43 | F3-PZ | .44 | .25 | .51 | C3-C4 | .44 | .51 | .44 | O1-T3 | .65 | .37 | .26 |
| FP1-P4 | .26 | .12 | .32 | F4-F7 | .39 | .50 | .46 | C3-P3 | .56 | .59 | .63 | O1-T4 | .22 | .16 | .19 |
| FP1-O1 | .25 | .09 | .20 | F4-F8 | .54 | .76 | .63 | C3-P4 | .46 | .34 | .39 | O1-T5 | .77 | .72 | .66 |
| FP1-O2 | .23 | .03 | .08 | FP4-C3 | .34 | .46 | .46 | C3-O1 | .43 | .33 | .32 | O1-T6 | .60 | .33 | .27 |
| FP1-T3 | .34 | .46 | .40 | F4-C4 | .54 | .54 | .50 | C3-O2 | .29 | .13 | .11 | O1-FZ | .40 | .15 | .26 |
| FP1-T4 | .21 | .25 | .32 | F4-P3 | .34 | .17 | .45 | C3-T3 | .53 | .55 | .38 | O1-CZ | .41 | .24 | .38 |
| FP1-T5 | .26 | .16 | .38 | F4-P4 | .41 | .20 | .44 | C3-T4 | .17 | .28 | .30 | O1-PZ | .66 | .58 | .60 |
| FP1-T6 | .24 | .06 | .24 | F4-O1 | .25 | .08 | .21 | C3-T5 | .41 | .44 | .53 | O2-T3 | .48 | .12 | .05 |
| FP1-FZ | N/A | .79 | .72 | F4-O2 | .23 | .04 | .11 | C3-T6 | .35 | .12 | .28 | O2-T4 | .29 | .19 | .19 |
| FP1-CZ | .32 | .45 | .53 | F4-T3 | .32 | .28 | .36 | C3-FZ | N/A | .60 | .64 | O2-T5 | .62 | .62 | .09 |
| FP1-PZ | .26 | .15 | .41 | F4-T4 | .35 | .45 | .43 | C3-CZ | .45 | .72 | .70 | O2-T6 | .64 | .65 | .74 |
| FP2-F3 | N/A | .60 | .59 | F4-T5 | .20 | .10 | .10 | C3-PZ | .52 | .53 | .56 | O2-FZ | N/A | .05 | .13 |
| FP2-F4 | N/A | .63 | .53 | F4-T6 | .29 | .09 | .33 | C4-P3 | .53 | .37 | .49 | O2-CZ | .35 | .14 | .23 |
| FP2-F7 | N/A | .54 | .48 | F4-FZ | .70 | .83 | .72 | C4-P4 | .65 | .57 | .63 | O2-PZ | .59 | .43 | .49 |
| FP2-F8 | N/A | .62 | .56 | F4-CZ | .52 | .60 | .67 | C4-O1 | .39 | .21 | .25 | T3-T4 | .25 | .17 | .24 |
| FP2-C3 | N/A | .37 | .46 | F4-PZ | .37 | .22 | .50 | C4-O2 | .38 | .19 | .21 | T3-T5 | .69 | .65 | .65 |
| FP2-C4 | N/A | .34 | .45 | F4-F8 | .36 | .41 | .35 | C4-T3 | .41 | .25 | .33 | T3-T6 | .41 | .08 | .19 |
| FP2-P3 | N/A | .11 | .43 | F7-C3 | .44 | .52 | .61 | C4-T4 | .48 | .62 | .40 | T3-FZ | .55 | .43 | .47 |
| FP2-P4 | N/A | .08 | .36 | F7-C4 | .36 | .29 | .38 | C4-T5 | .33 | .19 | .37 | T3-CZ | .45 | .35 | .47 |
| FP2-O1 | N/A | .06 | .20 | F7-P3 | .51 | .22 | .48 | C4-T6 | .48 | .31 | .46 | T3-PZ | .54 | .28 | .40 |
| FP2-O2 | N/A | .03 | .12 | F7-P4 | .37 | .10 | .30 | C4-FZ | .69 | .61 | .63 | T4-T5 | .18 | .11 | .26 |
| FP2-T3 | N/A | .30 | .37 | FP7-O1 | .42 | .14 | .20 | C4-CZ | .72 | .78 | .74 | T4-T6 | .33 | .42 | .39 |
| FP2-T4 | N/A | .26 | .38 | F7-O2 | .36 | .03 | .08 | C4-PZ | .62 | .54 | .63 | FP1-FZ | N/A | .36 | .43 |
| FP2-T5 | N/A | .09 | .36 | F7-T3 | .57 | .66 | .50 | P3-P4 | .67 | .56 | .59 | T4-CZ | .43 | .41 | .43 |
| FP2-T6 | N/A | .05 | .28 | F7-T4 | .29 | .17 | .27 | P3-O1 | .74 | .75 | .75 | T4-PZ | .33 | .30 | .43 |
| FP2-FZ | N/A | .72 | .72 | F7-T5 | .40 | .27 | .44 | P3-O2 | .61 | .36 | .24 | T5-T6 | .50 | .16 | .23 |
| FP2-CZ | N/A | .39 | .56 | F7-T6 | .29 | .04 | .21 | P3-T3 | .67 | .46 | .53 | T5-FZ | N/A | .21 | .48 |
| FP2-PZ | N/A | .10 | .43 | F7-FZ | N/A | .66 | .65 | P3-T4 | .26 | .20 | .34 | T5-CZ | .35 | .26 | .58 |
| F3-F4 | .52 | .65 | .53 | F7-CZ | .42 | .42 | .57 | P3-T5 | .71 | .73 | .85 | T5-PZ | .58 | .43 | .60 |
| F3-F7 | .53 | .76 | .81 | F7-PZ | .41 | .16 | .41 | P3-T6 | .55 | .26 | .41 | T6-FZ | .37 | .08 | .36 |
| F3-F8 | .46 | .54 | .45 | F8-C3 | .26 | .33 | .36 | P3-FZ | .51 | .27 | .58 | T6-CZ | .41 | .15 | .48 |
| FP3-C3 | .43 | .62 | .73 | F8-C4 | .53 | .54 | .53 | P3-CZ | .58 | .48 | .72 | T6-PZ | .59 | .37 | .69 |
| F3-C4 | .52 | .48 | .46 | FP8-P3 | .32 | .12 | .36 | P3-PZ | .78 | .79 | .83 | FZ-CZ | .80 | .71 | .80 |
| F3-P3 | .47 | .27 | .55 | F8-P4 | .36 | .16 | .37 | P4-O1 | .59 | .49 | .40 | FZ-PZ | .50 | .28 | .60 |
| F3-P4 | .41 | .18 | .37 | F8-O1 | .23 | .06 | .17 | P4-O2 | .59 | .62 | .69 | CZ-PZ | .68 | .62 | .80 |
| F3-O1 | .34 | .14 | .24 | F8-O2 | .15 | .02 | .10 | P4-T3 | .47 | .19 | .27 | | | | |

TABLE 2B

| Pair | Θ | α | β | Pair | Θ | α | β | Pair | Θ | α | β | Pair | Θ | α | β |
|---|---|---|---|---|---|---|---|---|---|---|---|---|---|---|---|
| FP1-FP2 | .60 | .78 | .66 | F3-O2 | .21 | .05 | .05 | F8-T3 | .18 | .14 | .02 | P4-T4 | .36 | .33 | .22 |
| FP1-F3 | .58 | .83 | .54 | F3-T3 | .48 | .43 | .03 | F8-T4 | .25 | .39 | .26 | P4-T5 | .46 | .26 | .30 |
| FP1-F4 | .42 | .62 | .36 | F3-T4 | .28 | .22 | .12 | F8-T5 | .13 | .05 | .13 | P4-T6 | .66 | .70 | .81 |

TABLE 2B-continued

| Pair | Θ | α | β | Pair | Θ | α | β | Pair | Θ | α | β | Pair | Θ | α | β |
|---|---|---|---|---|---|---|---|---|---|---|---|---|---|---|---|
| FP1-F7 | .44 | .75 | .44 | F3-T5 | .31 | .24 | .24 | F8-T6 | .14 | .05 | .14 | P4-FZ | .44 | .19 | .36 |
| FP1-F8 | .29 | .40 | .25 | F3-T6 | .23 | .06 | .14 | F8-FZ | .40 | .57 | .41 | P4-CZ | .62 | .45 | .54 |
| FP1-C3 | .45 | .57 | .26 | F3-FZ | .81 | .88 | .76 | F8-CZ | .30 | .39 | .33 | P4-PZ | .82 | .78 | .79 |
| FP1-C4 | .37 | .37 | .26 | F3-CZ | .62 | .63 | .60 | F8-PZ | .19 | .12 | .24 | O1-O2 | .72 | .49 | .13 |
| FP1-P3 | .32 | .20 | .25 | F3-PZ | .44 | .27 | .35 | C3-C4 | .67 | .59 | .30 | O1-T3 | .51 | .29 | .06 |
| FP1-P4 | .27 | .17 | .13 | F4-F7 | .41 | .47 | .25 | C3-P3 | .72 | .62 | .43 | O1-T4 | .22 | .08 | .06 |
| FP1-O1 | .24 | .10 | .10 | F4-F8 | .45 | .66 | .51 | C3-P4 | .56 | .33 | .22 | O1-T5 | .77 | .69 | .67 |
| FP1-O2 | .17 | .04 | .03 | FP4-C3 | .56 | .53 | .25 | C3-O1 | .45 | .31 | .13 | O1-T6 | .54 | .29 | .12 |
| FP1-T3 | .30 | .42 | .03 | F4-C4 | .67 | .68 | .62 | C3-O2 | .39 | .13 | .05 | O1-FZ | .26 | .10 | .16 |
| FP1-T4 | .23 | .19 | .10 | F4-P3 | .3 | .17 | .28 | C3-T3 | .53 | .55 | .01 | O1-CZ | .36 | .22 | .24 |
| FP1-T5 | .25 | .18 | .18 | F4-P4 | .38 | .17 | .30 | C3-T4 | .31 | .23 | .09 | O1-PZ | .63 | .51 | .52 |
| FP1-T6 | .18 | .06 | .10 | F4-O1 | .20 | .07 | .11 | C3-T5 | .52 | .44 | .23 | O2-T3 | .38 | .11 | .01 |
| FP1-FZ | .56 | .79 | .63 | F4-O2 | .18 | .03 | .07 | C3-T6 | .37 | .11 | .12 | O2-T4 | .24 | .11 | .08 |
| FP1-CZ | .37 | .46 | .38 | F4-T3 | .29 | .25 | .04 | C3-FZ | .71 | .70 | .52 | O2-T5 | .62 | .30 | .07 |
| FP1-PZ | .28 | .18 | .24 | F4-T4 | .36 | .40 | .25 | C3-CZ | .80 | .81 | .59 | O2-T6 | .67 | .65 | .72 |
| FP2-F3 | .47 | .70 | .45 | F4-T5 | .20 | .10 | .19 | C3-PZ | .67 | .54 | .36 | O2-FZ | .21 | .04 | .08 |
| FP2-F4 | .48 | .74 | .46 | F4-T6 | .23 | .07 | .18 | C4-P3 | .52 | .37 | .37 | O2-CZ | .35 | .13 | .16 |
| FP2-F7 | .33 | .55 | .32 | F4-FZ | .79 | .85 | .61 | C4-P4 | .63 | .53 | .54 | O2-PZ | .63 | .44 | .42 |
| FP2-F8 | .32 | .57 | .40 | F4-CZ | .59 | .63 | 52 | C4-O1 | .36 | .18 | .15 | T3-T4 | .21 | .10 | .02 |
| FP2-C3 | .34 | .47 | .21 | F4-PZ | .36 | .26 | .34 | C4-O2 | .36 | .16 | .16 | T3-T5 | .55 | .56 | .23 |
| FP2-C4 | .34 | .45 | .32 | F4-F8 | .24 | .30 | .17 | C4-T3 | .34 | .24 | .06 | T3-T6 | .31 | .09 | .02 |
| FP2-P3 | .25 | .16 | .26 | F7-C3 | .55 | .64 | .35 | C4-T4 | .45 | .57 | .31 | T3-FZ | .37 | .36 | .06 |
| FP2-P4 | .25 | .14 | .22 | F7-C4 | .37 | .20 | .23 | C4-T5 | .34 | .16 | .26 | T3-CZ | .39 | .34 | .06 |
| FP2-O1 | .22 | .07 | .11 | F7-P3 | .41 | .28 | .28 | C4-T6 | .45 | .37 | .21 | T3-PZ | .44 | .26 | .02 |
| FP2-O2 | .16 | .04 | .05 | F7-P4 | .28 | .12 | .16 | C4-FZ | .69 | .64 | .55 | T4-T5 | .21 | .06 | .10 |
| FP2-T3 | .23 | .20 | .04 | FP7-O1 | .31 | .16 | .11 | C4-CZ | .80 | .82 | .65 | T4-T6 | .31 | .28 | .12 |
| FP2-T4 | .23 | .27 | .16 | F7-O2 | .20 | .05 | .04 | C4-PZ | .62 | .55 | .51 | FP1-FZ | .30 | .31 | .20 |
| FP2-T5 | .22 | .11 | .19 | F7-T3 | .45 | .59 | .08 | P3-P4 | .67 | .53 | .48 | T4-CZ | .34 | .35 | .22 |
| FP2-T6 | .13 | .06 | .13 | F7-T4 | .19 | .13 | .09 | P3-O1 | .73 | .71 | .65 | T4-PZ | .33 | .23 | .20 |
| FP2-FZ | .51 | .80 | .61 | F7-T5 | .35 | .33 | .22 | P3-O2 | .64 | .38 | .18 | T5-T6 | .47 | .19 | .15 |
| FP2-CZ | .31 | .47 | .40 | F7-T6 | .17 | .06 | .10 | P3-T3 | .57 | .44 | .11 | T5-FZ | .25 | .16 | .29 |
| FP2-PZ | .24 | .18 | .29 | F7-FZ | .52 | .64 | .47 | P3-T4 | .28 | .15 | .14 | T5-CZ | .35 | .23 | .40 |
| F3-F4 | .62 | .69 | .41 | F7-CZ | .41 | .42 | .37 | P3-T5 | .74 | .74 | .78 | T5-PZ | .55 | .38 | .56 |
| F3-F7 | .57 | .78 | .54 | F7-PZ | .33 | .19 | .25 | P3-T6 | .52 | .28 | .26 | T6-FZ | .25 | .07 | .21 |
| F3-F8 | .33 | .43 | .26 | F8-C3 | .28 | .30 | .15 | P3-FZ | .44 | .25 | .47 | T6-CZ | .38 | .15 | .32 |
| FP3-C3 | .71 | .75 | .67 | F8-C4 | .39 | .47 | .41 | P3-CZ | .60 | .49 | .64 | T6-PZ | .55 | .36 | .53 |
| F3-C4 | .57 | .50 | .35 | FP8-P3 | .17 | .09 | .18 | P3-PZ | .81 | .76 | .80 | FZ-CZ | .71 | .74 | .76 |
| F3-P3 | .45 | .29 | .37 | F8-P4 | .20 | .10 | .22 | P4-O1 | .55 | .42 | .28 | FZ-PZ | .46 | .29 | .48 |
| F3-P4 | .38 | .16 | .24 | F8-O1 | .11 | .04 | .04 | P4-O2 | .64 | .63 | .69 | CZ-PZ | .69 | .64 | .71 |
| F3-O1 | .29 | .13 | .12 | F8-O2 | .12 | .02 | .06 | P4-T3 | .39 | .17 | .04 | | | | |

TABLE 3A

| Pair | Θ | α | β | Pair | Θ | α | β | Pair | Θ | α | β | Pair | Θ | α | β |
|---|---|---|---|---|---|---|---|---|---|---|---|---|---|---|---|
| FP1-FP2 | | 8% | 0% | F3-O2 | -22% | 0% | -44% | FP2-T5 | | 22% | -47% | F7-T3 | -21% | -11% | -84% |
| FP1-F3 | 45% | 9% | -19% | F3-T3 | -6% | -22% | -93% | FP2-T6 | | 20% | -54% | F7-T4 | -34% | -24% | -67% |
| FP1-F4 | 45% | -2% | -28% | F3-T4 | 0% | 0% | -21% | -65% | FP2-FZ | | 11% | -15% | F7-T5 | -13% | 22% | -50% |
| FP1-F7 | 19% | 1% | -27% | F3-T5 | -11% | 0% | -49% | FP2-CZ | | 21% | -29% | F7-T6 | -41% | 50% | -52% |
| FP1-F8 | | -29% | -39% | F3-T6 | -21% | 0% | -48% | PP2-PZ | | 80% | -33% | F7-FZ | | -3% | -28% |
| FP1-C3 | 45% | 19% | -46% | F3-FZ | 5% | 5% | 0% | F3-F4 | 19% | 6% | -23% | F7-CZ | -2% | 0% | -35% |
| FP1-C4 | 23% | 3% | -32% | F3-CZ | 5% | 2% | -13% | F3-F7 | 8% | 3% | -33% | F7-PZ | -20% | 19% | -39% |
| FP1-P3 | 10% | 25% | -42% | F3-PZ | 0% | 8% | -31% | F3-F8 | -28% | -20% | -42% | F8-C3 | 8% | -9% | -58% |
| FP1-P4 | 4% | 42% | -59% | F4-F7 | 5% | -6% | -46% | FP3-C3 | 65% | 21% | -8% | F8-C4 | -26% | -13% | -23% |
| FP1-O1 | -4% | 11% | -50% | F4-F8 | -17% | -13% | -19% | F3-C4 | 10% | 4% | -24% | FP8-P3 | -47% | -25% | -50% |
| FP1-O2 | -26% | 33% | -63% | FP4-C3 | 65% | 15% | -46% | F3-P3 | -4% | 7% | -33% | F8-P4 | -44% | -38% | -41% |
| FP1-T3 | -12% | -9% | -93% | F4-C4 | 24% | 26% | 15% | F3-P4 | -7% | -11% | -35% | F8-O1 | -52% | -33% | |
| FP1-T4 | 10% | -24% | -69% | F4-P3 | -12% | | -38% | F3-O1 | -15% | -7% | -50% | F8-O2 | -20% | 0% | -40% |
| FP1-T5 | -4% | 13% | -53% | F4-P4 | -7% | -15% | -32% | | | | | | | | |
| FP1-T6 | -25% | 0% | -58% | F4-O1 | -20% | -13% | -48% | | | | | | | | |
| FP1-FZ | | 0% | -13% | F4-O2 | -22% | -25% | -36% | | | | | | | | |
| FP1-CZ | 16% | 2% | -28% | F4-T3 | -9% | -11% | -89% | | | | | | | | |
| FP1-PZ | 8% | 20% | -41% | F4-T4 | 3% | -11% | -42% | | | | | | | | |
| FP2-F3 | | 17% | -24% | F4-T5 | 0% | 0% | 90% | | | | | | | | |
| FP2-F4 | | 17% | -13% | F4-T6 | -21% | -22% | -45% | | | | | | | | |
| FP2-F7 | | 2% | -33% | F4-FZ | 13% | 2% | -15% | | | | | | | | |
| FP2-F8 | | -8% | -29% | F4-CZ | 13% | 5% | 7661% | | | | | | | | |
| FP2-C3 | | 27% | -54% | F4-PZ | -3% | 18% | -32% | | TABLE 3B | | | | | | | |
| FP2-C4 | | 32% | -29% | F4-F8 | -33% | -27% | -51% | Pair | Θ | α | β | Pair | Θ | α | β |
| FP2-P3 | | 45% | -40% | F7-C3 | 25% | 23% | -43% | F8-T3 | -45% | -36% | -93% | P4-T4 | 0% | -25% | -49% |
| FP2-P4 | | 75% | -39% | F7-C4 | 3% | -31% | -39% | F8-T4 | -17% | -15% | -48% | P4-T5 | -4% | -13% | -17% |
| FP2-O1 | | 17% | -45% | F7-P3 | -20% | 27% | -42% | F8-T5 | -32% | -29% | -57% | P4-T6 | -1% | 0% | -8% |
| FP2-O2 | | 33% | -58% | F7-P4 | -24% | 20% | -47% | F8-T6 | -52% | -38% | -53% | P4-FZ | -12% | -10% | -25% |
| FP2-T3 | | -33% | -89% | FP7-O1 | -26% | 14% | -45% | F8-FZ | | -20% | -31% | P4-CZ | 0% | 2% | -18% |
| FP2-T4 | | 4% | -58% | F7-O2 | -44% | 67% | -50% | F8-CZ | -36% | -17% | -34% | P4-PZ | 5% | -1% | -8% |
| | | | | | | | | F8-PZ | -42% | -25% | -41% | O1-O2 | -3% | -2% | -43% |
| | | | | | | | | C3-C4 | 52% | 16% | -32% | O1-T3 | -22% | -22% | -77% |
| | | | | | | | | C3-P3 | | 5% | -32% | O1-T4 | | -50% | -68% |
| | | | | | | | | C3-P4 | 22% | -3% | -44% | O1-T5 | 0% | -4% | 2% |

TABLE 3B-continued

| Pair | Θ | α | β | Pair | Θ | α | β |
|---|---|---|---|---|---|---|---|
| C3-O1 | 5% | −6% | −59% | O1-T6 | −10% | −12% | −56% |
| C3-O2 | 34% | 0% | −55% | O1-FZ | −35% | −33% | −38% |
| C3-T3 | 0% | 0% | −97% | O1-CZ | −12% | −8% | −37% |
| C3-T4 | 82% | −18% | −70% | O1-PZ | −5% | −12% | −13% |
| C3-T5 | 27% | 0% | −57% | O2-T3 | −21% | −8% | −80% |
| C3-T6 | 6% | −8% | −57% | O2-T4 | −17% | −42% | −58% |
| C3-FZ |  | 17% | −19% | O2-T5 | 0% | −52% | −22% |
| C3-CZ | 78% | 13% | −16% | O2-T6 | 5% | 0% | −3% |
| C3-PZ | 29% | 2% | −36% | O2-FZ |  | −20% | −38% |
| C4-P3 | −2% | 0% | −24% | O2-CZ | 0% | −7% | −30% |
| C4-P4 | −3% | −7% | −14% | O2-PZ | 7% | 2% | −14% |
| C4-O1 | −8% | −14% | −40% | T3-T4 | −16% | −41% | −92% |
| C4-O2 | −5% | −16% | −24% | T3-T5 | −20% | −14% | −65% |
| C4-T3 | −17% | −4% | −82% | T3-T6 | −24% | 13% | −89% |
| C4-T4 | −6% | −8% | −23% | T3-FZ | −33% | −16% | −87% |
| C4-T5 | 3% | −16% | −30% | T3-CZ | −13% | −3% | −87% |
| C4-T6 | −6% | 19% |  | T3-PZ | −19% | −7% | −95% |
| C4-FZ | 0% | 5% | −13% | T4-T5 | 17% | −45% | −62% |
| C4-CZ | 11% | 5% | −12% | T4-T6 | −6% | −33% | −69% |
| C4-PZ | 0% | 2% | −19% | FP1-FZ |  | −14% | −53% |
| P3-P4 | 0% |  | −19% | T4-CZ | −21% | −15% | −49% |
| P3-O1 | −1% | −5% | −13% | T4-PZ | 0% | −23% | −53% |
| P3-O2 | 5% | 6% | −25% | T5-T6 | −6% | 19% | −35% |
| P3-T3 | −15% | −4% | −79% | T5-FZ |  | −24% | −40% |
| P3-T4 | 8% | −25% | −59% | T5-CZ | 0% | −12% | −31% |
| P3-T5 | 4% | 1% | −8% | T5-PZ | −5% | −12% | −7% |
| P3-T6 | −5% | 8% | −37% | T6-FZ | −32% | −13% | −42% |
| P3-FZ | −14% | −7% | −19% | T6-CZ | −7% | 0% | −33% |
| P3-CZ | 3% | 2% | −11% | T6-PZ | −7% | −3% | −23% |
| P3-PZ | 4% | −4% | −4% | FZ-CZ | −11% | 4% | −5% |
| P4-O1 | −7% | −14% | −30% | FZ-PZ | −8% | 4% | −20% |
| P4-O2 | 8% | 2% | 0% | CZ-PZ | 1% | 3% | −11% |
| P4-T3 | −17% | −11% | −85% |  |  |  |  |

Surprisingly, a single treatment with a composition of the inventive concept was effective to at least partially restore electrical activity in previously quiescent portions of the brain of an individual that had suffered a significant left side stroke. The effect was rapid (occurring within 20 minutes), and the individual reported no untoward side effects. Without wishing to be bound by theory, the Inventors believe that compositions of the inventive concept quickly and effectively cross the blood brain barrier, and in doing so provide transport for compounds that are effective in increasing activity of quiescent neurons. Inventors believe that application of compositions of the inventive concept can be useful in the recovery of individuals that have suffered brain injury, for example due to stroke, disease, or injury.

Example 2

Figure 8A:
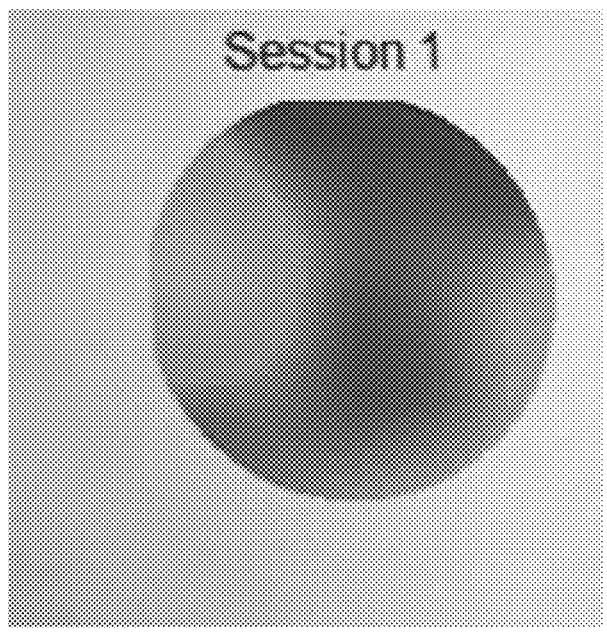
FIGS. 8A and 8B.
Figure 8B:
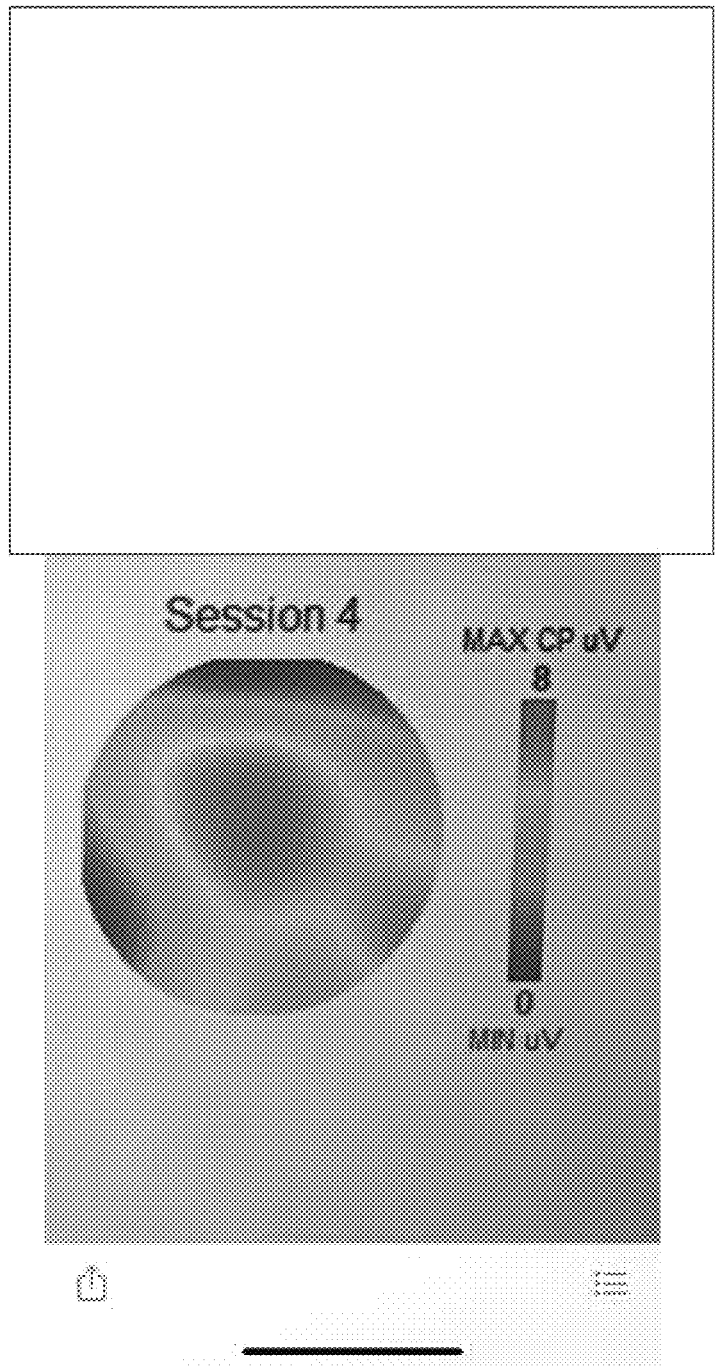

An 8 year old male clinically diagnosed with autism showed with profound issues with social interactions was treated with a formulation of the inventive concept. Without treatment the family had found it necessary to restrain him in most social events. He showed anger toward strangers, and had poor verbal skills and understanding after years of conventional treatment. FIG. 8A shows results of a brain activity scan obtained prior to treatment. Within 30 minutes of oral administration of about 28 grams of a formulation of the inventive concept the child was able to respond to a brain scan reaction test with clarity. Said scan showed a general increase in brain activity. In addition, mood issues and aggression were markedly reduced following administration of a single dose. FIG. 8B shows results of a brain activity scan obtained 30 minutes following treatment with a single dose of a formulation of the inventive concept. Notably, prior treatment using only the ketone portion of the formulation had no apparent effect.

Example 3

A 54 year old female with a diagnosis of traumatic brain injury due to severe impact was treated with a formulation of the inventive concept. This individual had been hospitalized for several weeks due to severity of the injury, and has had short term memory issues requiring the preparation of a daily schedule to assist in normal tasks for several years. Following treatment with a single 28 gram dose of a formulation of the inventive concept she reported a sensation of increased clarity, and reported that. colors appeared to be brighter, smells more distinct, and touch more sensitive. On testing a dramatic decrease in reaction time was noted.

Example 4

An 18 month old Irish wolfhound with Steroid Responsive Meningitis-Arteritis (SRMA) was found to symptomatically improve significantly more rapidly than anticipated when treated with a formulation of the inventive concept to augment traditional treatments. No adverse symptoms were recorded during the 12 days of treatment and the dog continued to improve throughout the course of supplementation.

In addition to treatment of central nervous system disorders, Inventors contemplate that compositions and formulations of the inventive concept can be effective at improving athletic performance. Examples of improved athletic performance include enhanced agility, reduced response time, improved accuracy, and increased speed. Similarly, Inventors contemplate that compositions and formulations of the inventive concept can be effective in reducing recovery time following physical exertion, such as from an athletic event.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of increasing activity in damaged or quiescent central nervous system neurons, comprising orally administering, to an individual in need of treatment for a central nervous system condition, a composition comprising:
  orally administering a formulation comprising a water-soluble fullerene and a ketone at a baseline dosage of from 0.01 mg/kg to 1 g/kg, wherein the molar ratio of the water soluble fullerene to the ketone is from 1:1 to 1:50,000;
  wherein the water-soluble fullerene and the ketone are provided in a ratio effective to increase activity in a quiescent neuron of the individual's central nervous system within 20 minutes.

2. The method of claim 1, wherein the ketone is reversibly coupled to the water-soluble fullerene.

3. The method of claim 1, wherein the ketone is covalently coupled to the water-soluble fullerene.

4. The method of claim 1, wherein the ketone is encapsulated by the water-soluble fullerene.

5. The method of claim 1, wherein the individual in need of treatment has a condition selected from the group consisting of a stroke, a cerebrovascular accident, and traumatic brain injury.

6. The method of claim 1, further comprising:
evaluating the effect of the baseline dosage on the central nervous system condition of the individual in need of treatment; and
adjusting the baseline dosage of the formulation to be orally administered to the individual in need of treatment.

7. The method of claim 1, wherein the ketone is a ketone body compound.

* * * * *